United States Patent
Leibel

(10) Patent No.: US 9,636,228 B2
(45) Date of Patent: May 2, 2017

(54) RADIAL HEAD IMPLANT

(75) Inventor: David A. Leibel, Princeton, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 569 days.

(21) Appl. No.: 12/029,429

(22) Filed: Feb. 11, 2008

(65) Prior Publication Data

US 2008/0288079 A1    Nov. 20, 2008

Related U.S. Application Data

(60) Provisional application No. 60/889,267, filed on Feb. 10, 2007.

(51) Int. Cl.
| | | |
|---|---|---|
| A61F 2/38 | (2006.01) | |
| A61F 2/46 | (2006.01) | |
| A61B 17/56 | (2006.01) | |
| A61F 2/30 | (2006.01) | |

(52) U.S. Cl.
CPC .......... *A61F 2/3804* (2013.01); *A61F 2/4637* (2013.01); *A61F 2/4605* (2013.01); *A61F 2002/305* (2013.01); *A61F 2002/30387* (2013.01); *A61F 2002/30428* (2013.01); *A61F 2002/30481* (2013.01); *A61F 2002/30494* (2013.01); *A61F 2002/30505* (2013.01); *A61F 2002/30576* (2013.01); *A61F 2002/3827* (2013.01)

(58) Field of Classification Search
CPC ..................................... A61F 2/38; A61F 2/42
USPC ..................... 623/20.11–20.13, 21.11–21.13; 31/20.11–20.13
See application file for complete search history.

(56) References Cited

U.S. PATENT DOCUMENTS

| | | |
|---|---|---|
| 3,651,521 A | 3/1972 | Devas |
| 3,707,006 A | 12/1972 | Bokros et al. |
| 3,708,805 A | 1/1973 | Scales et al. |
| 3,813,699 A | 6/1974 | Giliberty |
| 3,863,273 A | 2/1975 | Averill |
| 3,868,730 A | 3/1975 | Kaufer et al. |
| 3,874,003 A | 4/1975 | Moser et al. |
| 3,924,276 A | 12/1975 | Eaton |
| 4,079,469 A | 3/1978 | Wadsworth |
| 4,106,128 A | 8/1978 | Greenwald |
| 4,106,130 A | 8/1978 | Scales |
| 4,131,957 A | 1/1979 | Bokros |
| 4,172,296 A | 10/1979 | D'Errico |
| 4,183,104 A | 1/1980 | Frey |

(Continued)

FOREIGN PATENT DOCUMENTS

| | | |
|---|---|---|
| DE | 4331262 A1 | 3/1995 |
| GB | 1567007 A | 5/1980 |
| JP | 4170948 B2 | 10/2008 |

OTHER PUBLICATIONS

International Search Report and Written Opinion for International Patent Application No. PCT/US2008/053606, dated Aug. 15, 2008.

(Continued)

*Primary Examiner* — Marcia Watkins
(74) *Attorney, Agent, or Firm* — Lerner, David, Littenberg, Krumholz & Mentlik, LLP

(57) ABSTRACT

A radial head implant including a head, a stem, and a locking mechanism, whereby the head laterally engages the stem, and an instrument for implanting and removing such implant is described.

30 Claims, 9 Drawing Sheets

(56) References Cited

U.S. PATENT DOCUMENTS

| | | |
|---|---|---|
| 4,187,559 A | 2/1980 | Grell |
| 4,224,695 A | 9/1980 | Grundei |
| 4,227,265 A | 10/1980 | Frey |
| 4,231,121 A | 11/1980 | Lewis |
| 4,241,463 A | 12/1980 | Khovaylo |
| 4,242,768 A | 1/1981 | Winsett |
| 4,257,129 A | 3/1981 | Volz |
| 4,259,752 A | 4/1981 | Taleisnik |
| 4,301,552 A | 11/1981 | London |
| 4,309,778 A | 1/1982 | Buechel et al. |
| 4,355,427 A | 10/1982 | Schneider |
| 4,378,607 A | 4/1983 | Wadsworth |
| 4,383,337 A | 5/1983 | Volz |
| 4,624,250 A | 11/1986 | Saunders |
| 4,718,414 A | 1/1988 | Saunders |
| 4,755,185 A | 7/1988 | Tarr |
| 4,770,661 A | 9/1988 | Oh |
| 4,784,663 A | 11/1988 | Kenna |
| 4,801,301 A | 1/1989 | Noiles |
| 4,822,364 A | 4/1989 | Inglis |
| 4,865,605 A | 9/1989 | Dines et al. |
| 4,913,144 A | 4/1990 | Del Medico et al. |
| 4,923,472 A | 5/1990 | Ugolini |
| 4,960,427 A | 10/1990 | Noiles |
| 5,024,670 A | 6/1991 | Smith |
| 5,030,237 A | 7/1991 | Sorbie |
| 5,108,442 A * | 4/1992 | Smith ............... 623/20.33 |
| 5,147,388 A | 9/1992 | Yamazaki |
| 5,201,881 A | 4/1993 | Evans |
| 5,429,641 A | 7/1995 | Gotfried |
| 5,458,637 A | 10/1995 | Hayes |
| 5,458,648 A | 10/1995 | Berman et al. |
| 5,462,563 A | 10/1995 | Shearer |
| 5,489,309 A | 2/1996 | Lackey et al. |
| 5,527,182 A | 6/1996 | Willoughby |
| 5,527,342 A | 6/1996 | Pietrzak et al. |
| 5,529,736 A | 6/1996 | Shalaby |
| 5,549,681 A | 8/1996 | Segmuller |
| 5,702,463 A | 12/1997 | Pothier et al. |
| 5,725,585 A | 3/1998 | Zobel |
| 5,776,202 A | 7/1998 | Copf |
| 5,782,922 A | 7/1998 | Vandewalle |
| 5,782,923 A | 7/1998 | Engelbrecht |
| 5,824,103 A | 10/1998 | Williams |
| 5,824,108 A | 10/1998 | Huebner |
| 5,879,388 A | 3/1999 | Pienkowski |
| 5,879,395 A | 3/1999 | Tornier |
| 5,888,211 A | 3/1999 | Sanders |
| 5,906,210 A | 5/1999 | Herbert |
| 5,910,171 A | 6/1999 | Kummer |
| 5,961,555 A | 10/1999 | Huebner |
| 6,051,751 A | 4/2000 | Sioshansi |
| 6,059,830 A | 5/2000 | Lippincott, III |
| 6,096,083 A | 8/2000 | Keller |
| 6,126,695 A | 10/2000 | Semlitsch |
| 6,127,596 A | 10/2000 | Brown et al. |
| 6,159,247 A | 12/2000 | Klawitter |
| 6,162,253 A | 12/2000 | Conzemius |
| 6,217,615 B1 | 4/2001 | Sioshansi |
| 6,217,616 B1 | 4/2001 | Ogilvie |
| 6,228,119 B1 | 5/2001 | Ondrla |
| 6,270,503 B1 | 8/2001 | Schmieding |
| 6,270,529 B1 | 8/2001 | Terrill-Grisoni |
| 6,281,264 B1 | 8/2001 | Salovey |
| 6,290,725 B1 | 9/2001 | Weiss et al. |
| 6,299,645 B1 | 10/2001 | Ogden |
| 6,306,171 B1 | 10/2001 | Conzemius |
| 6,361,563 B2 | 3/2002 | Terrill-Grisoni |
| 6,379,388 B1 | 4/2002 | Ensign et al. |
| 6,425,921 B1 | 7/2002 | Grundei |
| 6,527,808 B1 | 3/2003 | Albertorio et al. |
| 6,547,824 B1 | 4/2003 | Price |
| 6,656,225 B2 * | 12/2003 | Martin ............... 623/20.12 |
| 6,679,916 B1 | 1/2004 | Frankle |
| 6,709,459 B1 | 3/2004 | Cooney, III et al. |
| 6,709,461 B2 | 3/2004 | O'Neil et al. |
| 6,767,368 B2 | 7/2004 | Tornier |
| 6,811,568 B2 | 11/2004 | Minamikawa |
| 6,818,019 B2 | 11/2004 | Horber |
| 6,953,478 B2 | 10/2005 | Bouttens |
| 7,160,329 B2 | 1/2007 | Cooney, III |
| 7,160,331 B2 | 1/2007 | Cooney, III |
| 7,169,186 B2 | 1/2007 | Harris et al. |
| 7,238,207 B2 | 7/2007 | Blatter et al. |
| 7,247,170 B2 | 7/2007 | Graham et al. |
| 7,452,381 B2 | 11/2008 | Steinmann |
| 7,608,110 B2 | 10/2009 | O'Driscoll |
| 7,641,698 B1 * | 1/2010 | Gibbs et al. ............... 623/22.15 |
| 7,662,185 B2 | 2/2010 | Alfaro et al. |
| 7,740,661 B2 | 6/2010 | Baratz et al. |
| 7,749,277 B2 | 7/2010 | McLean |
| 7,799,086 B2 | 9/2010 | Justin et al. |
| 7,875,082 B2 | 1/2011 | Naidu |
| 8,034,116 B2 | 10/2011 | Vander Meulen et al. |
| 8,066,779 B2 | 11/2011 | Gibbs et al. |
| 8,110,005 B2 | 2/2012 | Berelsman et al. |
| 8,114,163 B2 | 2/2012 | Berelsman et al. |
| 8,366,781 B2 | 2/2013 | Berelsman et al. |
| 8,425,615 B2 | 4/2013 | Berelsman et al. |
| 8,535,382 B2 | 9/2013 | Kehres et al. |
| 2002/0065561 A1 | 5/2002 | Ogilvie |
| 2003/0040805 A1 | 2/2003 | Minamikawa |
| 2003/0093156 A1 | 5/2003 | Metzger |
| 2003/0208276 A1 | 11/2003 | Berelsman |
| 2003/0208280 A1 | 11/2003 | Tohidi |
| 2004/0030394 A1 | 2/2004 | Horber |
| 2004/0078083 A1 | 4/2004 | Gibbs |
| 2004/0122519 A1 | 6/2004 | Wiley |
| 2004/0220678 A1 | 11/2004 | Chow |
| 2004/0220679 A1 | 11/2004 | Diaz |
| 2005/0033436 A1 | 2/2005 | Schlapfer |
| 2005/0033442 A1 | 2/2005 | Fisher |
| 2005/0049710 A1 | 3/2005 | O'Driscoll |
| 2005/0075735 A1 | 4/2005 | Berelsman |
| 2005/0216090 A1 | 9/2005 | O'Driscoll |
| 2006/0064173 A1 | 3/2006 | Guederian |
| 2006/0142866 A1 | 6/2006 | Baratz |
| 2006/0173546 A1 | 8/2006 | Berelsman et al. |
| 2006/0229732 A1 | 10/2006 | Bachelier |
| 2007/0073409 A1 | 3/2007 | Cooney, III et al. |
| 2007/0142919 A1 | 6/2007 | Cooney, III |
| 2008/0288079 A1 | 11/2008 | Leibel |
| 2010/0087928 A1 | 4/2010 | Graham et al. |
| 2010/0241236 A1 | 9/2010 | Katrana et al. |
| 2011/0144759 A1 | 6/2011 | Berelsman et al. |
| 2012/0109323 A1 | 5/2012 | Berelsman et al. |
| 2012/0221113 A1 | 8/2012 | Katrana et al. |
| 2013/0333198 A1 | 12/2013 | Kehres et al. |

OTHER PUBLICATIONS

Judet, T. et al., "Radial-head Prosthesis Indications and Techniques" [online], [retrieved Jul. 9, 2004]. Retrieved from Internet: URL : http://www.maitrise-orthop.com/corpusmaitri/orthopaedic/mo77_juet/index_us.shtml>.

"Liverpool(TM) Radial Head Replacement, Operative Technique," BIOMET Orthopedics, Inc., copyright 2002.

"rHead(TM) Recon Radial Implant System, Surgical Technique," Avanta Orthopaedics, copyright 2002.

"Swanson Titanium Radial Head Implant, Surgical Technique," Wright Medical Technology, Inc., copyright 2002.

International Search Report dated Aug. 15, 2008 for PCT/US2008/053606.

Small Bones Innovations, Inc., rHead™ Family Radial Head Implant System, 2009.

* cited by examiner

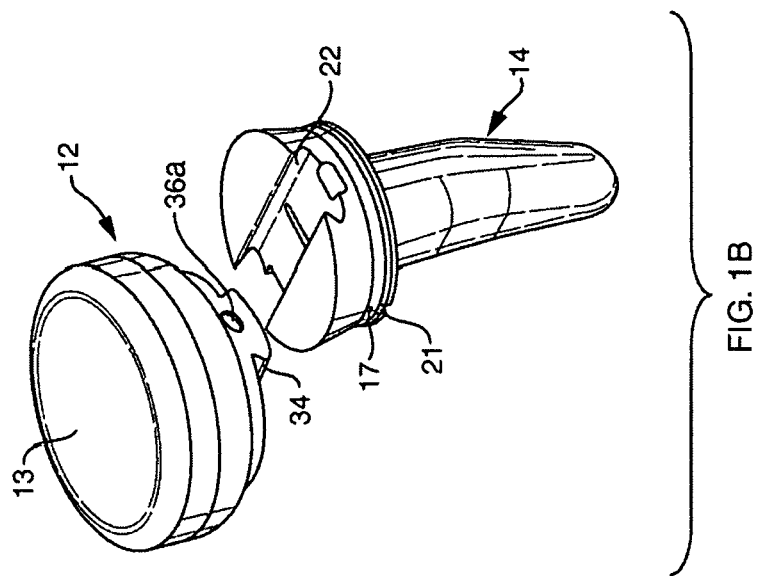
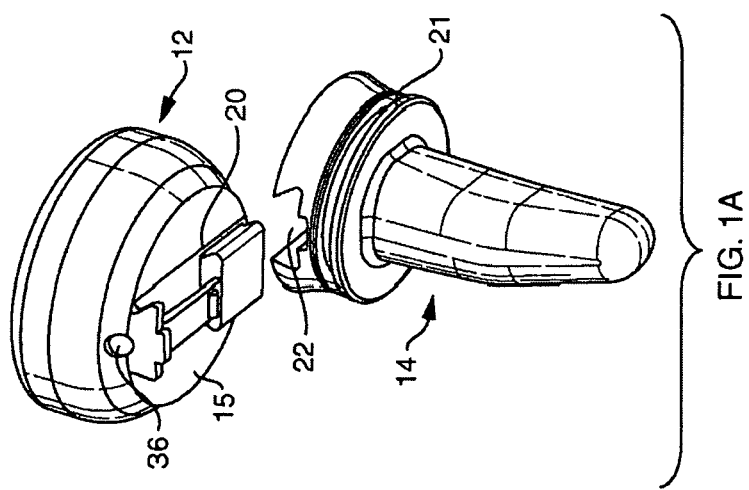

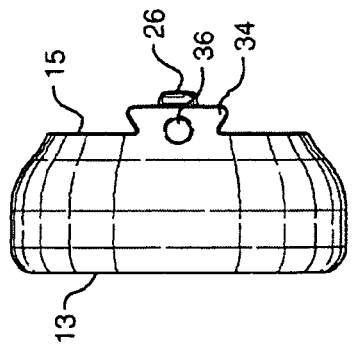
FIG. 3C
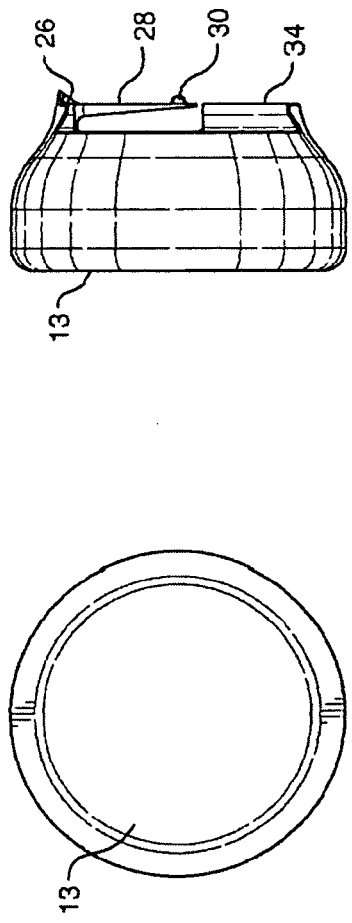
FIG. 3B
FIG. 3A
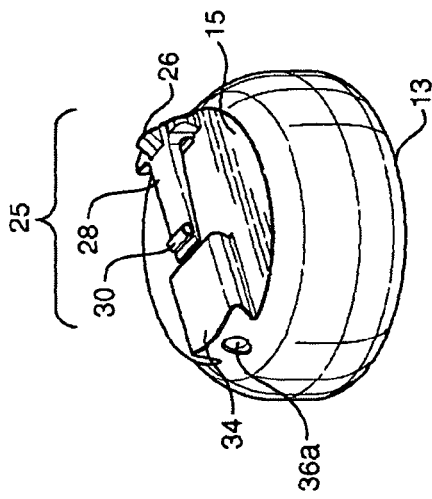
FIG. 3F
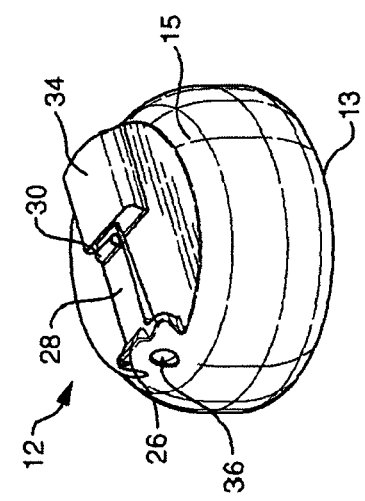
FIG. 3E
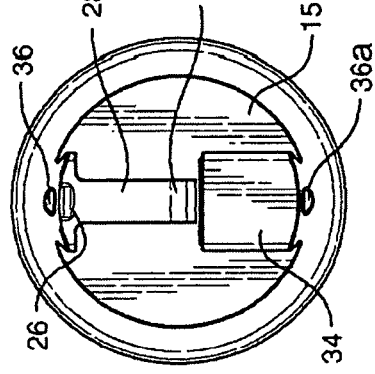
FIG. 3D

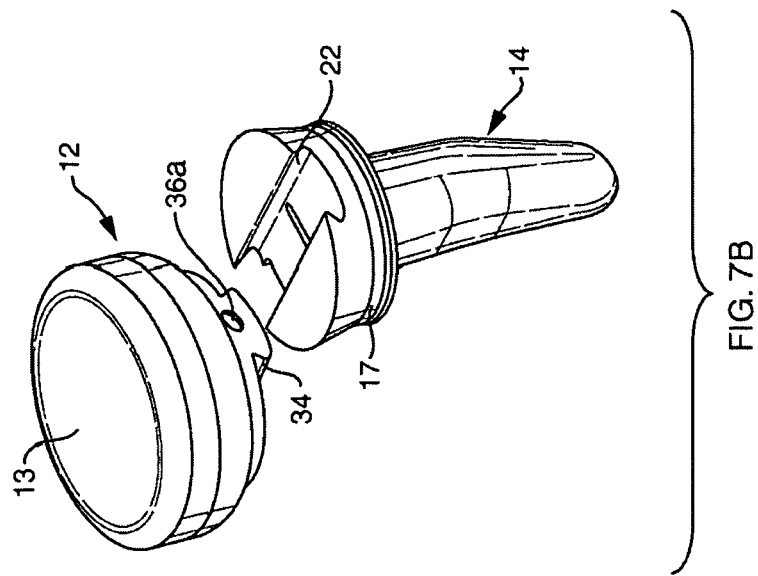
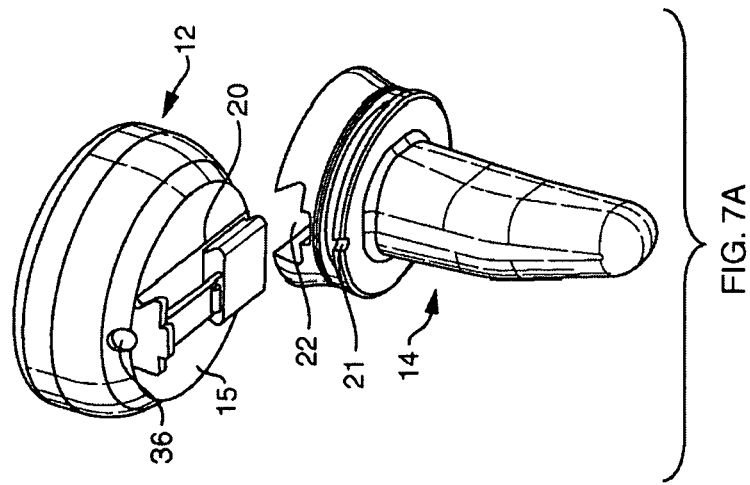

RADIAL HEAD IMPLANT

CROSS-REFERENCE TO RELATED APPLICATIONS

This application claims the benefit of provisional Application No. 60/889,267, filed 10 Feb. 2007, which is hereby incorporated by reference in its entirety.

BACKGROUND OF THE INVENTION

Like other joints and anatomical features of the human body, the elbow joint is complex in its make-up and function. Also like the other joints and anatomical features of the human body, the elbow joint is unique unto itself and requires specific consideration for its reconstruction or replacement. The complexity and uniqueness of this joint are best appreciated by considering the skeletal motions which are involved in its movement.

In the transition of the hand and forearm from pronation to supination the radius and ulna of the forearm transition from a crossed relationship to a side-by-side relationship. In this movement there is a relative rotation of the radius bone about the ulna. Also during the transition between pronation and supination there is some relative translational movement between the radius bone and the ulna. The consequence of this is that from a reference point on the ulna, the radius bone appears to move with a general motion that includes both translation and rotation. The head of the radius interacts with the capitellum and the radial notch of the ulna during pronation and supination, providing elbow and forearm stability during rotation and translation.

In addition to its importance as a component of forearm function, the radial head is an equally important component of normal elbow function. Indeed, elbow function involves bending, lifting and twisting movements, all of which require joint stability. Because motions in the human body require the interaction of various anatomical components, it is important that replacement of a component be precise in form, size, and orientation. While the head of the radius bone directly engages the capitellum of the humerus and the radial notch of the ulna, it also relates indirectly to other anatomical components of the arm. Specifically, ligaments surrounding the radial head are essential to elbow stability. Further, misalignment of the radius bone will cause poor radial-capitellar joint contact, leading to subluxation, or poor alignment of the elbow. It follows that the wrist and shoulder joints are also affected by the alignment of the radius bone.

The importance of having a workable prosthesis for the head of the radius bone is underscored by the debilitating effects which commonly result when a joint becomes damaged due to fracture, arthritis, or osteochondrosis. It is well known that radial head resection, as seen in elbow injuries, results in persistent elbow instability. Additionally, forearm axial instability can result from radial head excision if the remaining stabilizers, i.e., the supporting ligaments, are compromised. Because this loss of stability affects the interdependent functions of the elbow and forearm, when the radial head is damaged, it is common to see further damage to other components of the radial-ulnar joint system, including, but not limited to, the complex system of supporting ligaments that encase the elbow joint. It has been well demonstrated that damage to any one of the components of the radial-ulnar joint system leads to pain, weakness, and loss of motion. It is, therefore, of great importance to the patient that damage to the radial head be remedied.

SUMMARY OF THE INVENTION

The present invention includes a radial head implant for replacement of a head portion of a radius bone. In an embodiment of the invention, the implant includes a head, a stem, and a locking mechanism. In another embodiment, the head is adapted to engage the stem. In another embodiment, the locking mechanism includes an arm, a locking tab and an end tab.

In one embodiment, the head is adapted to slideably engage the stem. In an embodiment of the invention, the head is adapted to lockingly engage the stem. In another embodiment of the invention, the implant head is adapted to unlock and disengage from the stem after engagement and locking.

In an embodiment of the invention, the stem has (1) a proximal end and a distal end, (2) a first portion extending distally from the proximal end substantially along a first axis, and (3) a second portion extending distally from the first portion substantially along a second axis to the distal end, the first axis and the second axis defining an angle therebetween, the stem being shaped to facilitate insertion of said stem into the medullary canal of the radius bone. In an embodiment of the invention, the angle is from about 0 degrees to about 25 degrees. In an embodiment of the invention, the radius of curvature between the first portion and the second portion is in a range between about 0.5 inches and about 3 inches.

In an embodiment of the invention, the surface of the head includes a highly polished cobalt chrome to facilitate articulation of the radius bone. In another embodiment, the stem includes a roughened surface, for interaction with the medullary canal of the radius bone.

In an embodiment of the invention, the stem is tapered with a distally decreasing cross section to facilitate insertion of the stem into the medullary canal of the radius bone. In another embodiment, the stem includes a collar positioned on a first portion of said stem to limit insertion of said stem into the medullary canal of the radius bone.

In another embodiment of the present invention, the stem comprises a recessed channel adapted to engage said head. In one embodiment, the recessed channel is positioned along a third axis substantially perpendicular to the first axis of the stem. In an embodiment of the invention, the head includes a mating portion. In another embodiment, the recessed channel is adapted to engage the mating portion by way of a dovetail interaction between said mating portion and the recessed channel.

In an embodiment of the invention, a radial head implant for replacement of a head portion of a radius bone having a head and a stem is described. In one embodiment, the head has a locking mechanism adapted to engage the stem with the head. In another embodiment, the recessed channel is adapted to engage the locking mechanism.

In an embodiment of the invention, a radial head implant includes a head component having a proximal surface including a substantially concave recess configured to articulate with a capitellum of a humerus bone, a stem component engageable with the head component, and a securement configured to lock and unlock the stem component to the head component. In some embodiments, the securement includes a longitudinal channel having a first end, a second end, an end notch disposed at the second end, and a tab notch disposed at a position between the first end and the second end. In some embodiments, the securement further includes a mating portion engageable with the longitudinal channel in a dovetail interaction such that the mating portion is positioned in the longitudinal channel between the first end and the tab notch when the head component is locked to the stem component. In some embodiments, the securement further includes a cantilever spring arm disposable within the longitudinal channel such that the cantilever spring arm extends substantially along a centerline of the longitudinal channel from the tab notch to the second end when the head component is locked to the stem component, the cantilever spring arm having an end tab, proximate a fixed end of the cantilever spring arm, that is configured to be received in the end notch and having a locking tab, proximate a free end of the cantilever spring arm, that is configured to be received in the tab notch when the end tab is received in the end notch, each of the end tab and the locking tab protruding from the cantilever spring arm in a direction that is substantially transverse to the longitudinal channel when the head component is secured to the stem component. In some embodiments, the cantilever spring arm is tapered from the fixed end to the free end.

In another embodiment of the invention, an instrument for implanting a radial head implant is described. In one embodiment, the instrument includes a hook mechanism, at least two handles, a lever, and a first mating portion. In one embodiment, the hook mechanism is adapted to engage a groove on the stem. In another embodiment, the first mating portion is adapted to engage a second mating portion on the head of the implant.

In an embodiment of the present invention, a method for engaging a head and stem of a radial implant is described. In one embodiment, the method includes engaging the hook mechanism with the groove on the stem. In another embodiment, the method includes engaging the first mating portion with the second mating portion. In another embodiment, the method includes applying opposing pressure to the handles.

In an embodiment of the invention, a radial head implant for replacement of a head portion of a radius bone that includes a head, a stem, and a locking mechanism is described. In one embodiment, the head is adapted to engage the stem by way of a dovetail interaction between the head and the stem. In another embodiment, the head includes a mating portion and the stem includes a recessed channel. In one embodiment, the mating portion is adapted to engage the recessed channel by way of a dovetail interaction. In an embodiment of the invention, the mating portion includes an angle α, defining the angle between distal surface 15 of the head and a side of the mating portion. In another embodiment, the recessed channel includes an angle, β, defining an angle between the proximal side of the stem and a side of the recessed channel. In another embodiment, the angles α and β are substantially equal.

BRIEF DESCRIPTION OF THE DRAWINGS

FIG. 1, comprising FIGS. 1A and 1B, is an isometric view of a radial implant according to the present invention. FIG. 1A illustrates a front view of engagement of the head and stem portions of a radial implant according to the present invention. FIG. 1B illustrates a rear view of engagement of the head and stem portions of a radial implant according to the present invention.

FIG. 2, comprising FIG. 2A illustrates a front view of the radial implant. Cross section 2B-2B, identified in FIG. 2A is depicted in FIG. 2B. Detail 2C, identified in FIG. 2B is illustrated in FIG. 2C.

FIG. 3, comprising FIGS. 3A-3F, illustrates different views of a head portion of a radial implant according to the present invention. FIG. 3A illustrates a top view of a head portion of a radial implant according to the present invention. FIG. 3B is a side view of a head portion of a radial implant according to the present invention. FIG. 3C is a side view (which is about 90 degrees from the view shown in FIG. 3B) of a head portion of a radial implant according to the present invention. FIG. 3D is a bottom view of a head portion of a radial implant according to the present invention. FIGS. 3E and 3F are isometric views of a head portion of a radial implant according to the present invention.

FIG. 4, comprising FIG. 4A is a top view of a stem portion of a radial implant according to the present invention. FIG. 4B is a side view of a stem portion of a radial implant according to the present invention. FIG. 4C is a side view (which is about 90 degrees from the view shown in FIG. 3B) of a stem portion of a radial implant according to the present invention.

FIG. 6, comprising FIG. 6A is a rear isometric view of an instrument according to the present invention engaging the head and stem portions of a radial implant according to the present invention. FIG. 6B is another rear isometric view of an instrument according to the present invention. FIG. 6C is a slightly magnified view of the hook and lever mechanisms of an instrument according to the present invention. FIG. 6D is a front isometric view of an instrument according to the present invention.

FIG. 7, comprising FIGS. 7A and 7B, is an isometric view of an embodiment of a radial implant according to the present invention. In FIG. 7A, a front isometric view of engagement of the head and the stem portions of an embodiment of the radial implant is shown. FIG. 7B is a rear isometric view of engagement of the head and the stem portions of an embodiment of the radial implant is shown.

FIG. 8, comprising In FIG. 8A, a front view of an embodiment of the radial implant is shown. In FIG. 8B, a cross sectional view of the radial implant along the cutting plane line 8B-8B identified in FIG. 8A is shown. In FIG. 8C, Detail 8C, identified in FIG. 8B, is shown.

FIG. 9, comprising In FIG. 9A, a top view of an embodiment of the head portion 12 is shown. In FIG. 9B, a side view of an embodiment of the head portion is shown. In FIG. 9C, a side view (which is about 90 degrees from the view shown in FIG. 9B) of an embodiment of the head portion is shown. In FIG. 9D, a bottom view of an embodiment of the head portion is shown. In FIG. 9E, a front isometric view of an embodiment of the head portion is shown. In FIG. 9F, a rear isometric view (which is rotated 180 degrees from the view shown in FIG. 9E) of an embodiment of the head portion is shown.

FIG. 10, comprising In FIG. 10A, a top view of an embodiment of the stem portion is shown. In FIG. 10B, a side view of an embodiment of the stem portion is shown. In FIG. 10C, a side view (that is rotated 90° from the view shown in FIG. 10 B) of an embodiment of the stem portion is shown.

DETAILED DESCRIPTION

Figure 2C:
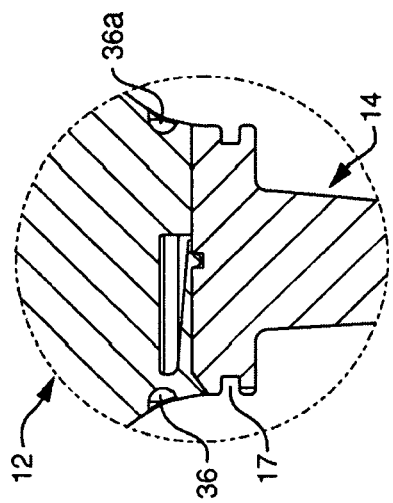
FIGS. 2A, 2B, and 2C, illustrates a cross sectional view of a radial implant according to the present invention.

Listing of Reference Numerals
10—radial head implant
12—head portion
13—proximal surface of head portion
14—stem portion
15—distal surface of head portion
16—first stem portion
17—groove
18—second stem portion
19—collar
20—mounting portion
21—orientation marker
22—recessed channel
24—end notch
25—locking mechanism
26—end tab
28—arm
30—locking tab
32—locking tab notch
34—mating portion
36, 36a—female mating dimple of head 12
38—instrument
40—fixed instrument handle
42—movable instrument handle
44—sliding lever
46—hook mechanism
48—male mating portion of lever 44
100—first axis
101—second axis

DETAILED DESCRIPTION

The present invention relates to a radial head implant 10 having a head portion 12 and a stem portion 14, head 12 adapted to engage stem 14 through a mounting portion 20. For purposes of this disclosure, and specifically for relative directional references between components of the present invention, head 12 is considered to be proximal to stem 14. Accordingly, stem 14 is considered to be distal to head 12.

Figure 2B:
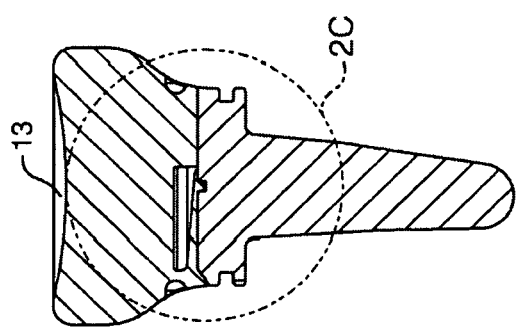
Figure 2A:
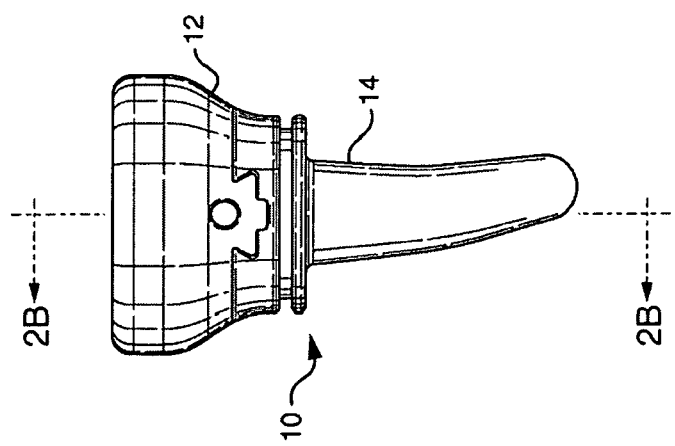
Figure 4B:
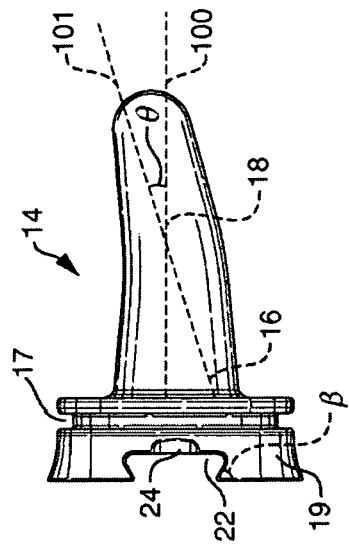
FIGS. 4A-4C, illustrates different views of a stem portion of a radial implant according to the present invention.
Figure 5:
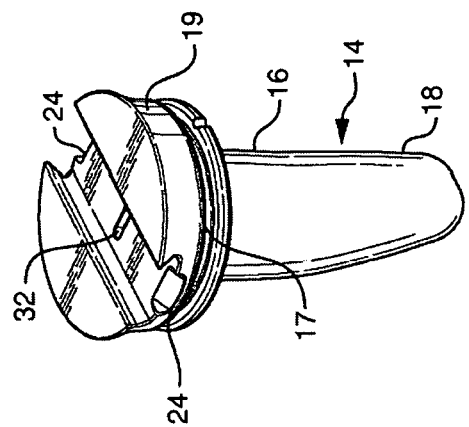
FIG. 5 illustrates an isometric view of a stem portion of a radial implant according to the present invention.
Figure 4A:
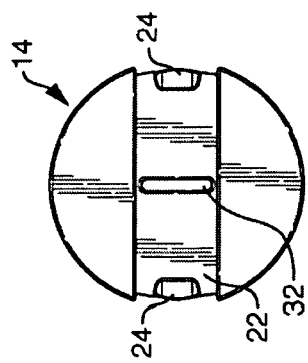
Figure 4C:
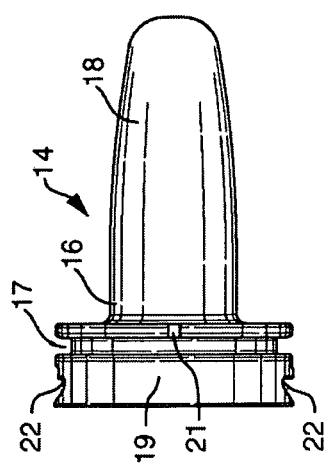
Figure 8C:
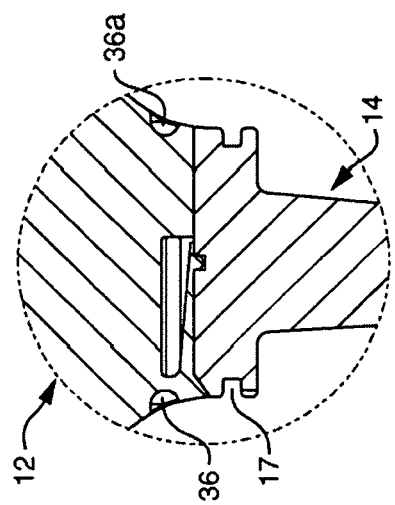
FIGS. 8A-8C, illustrates different views of an embodiment of a radial implant according to the present invention.
Figure 8B:
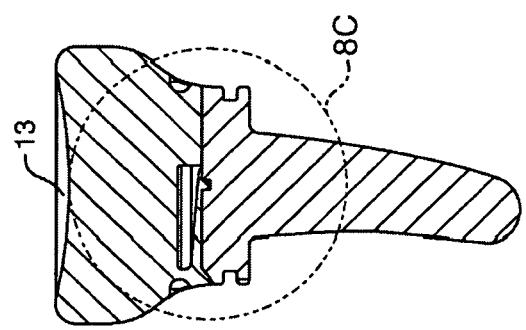
Figure 8A:
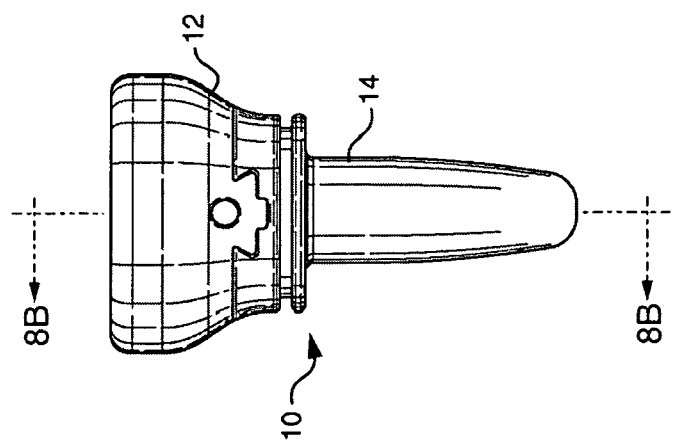
Figure 9C:
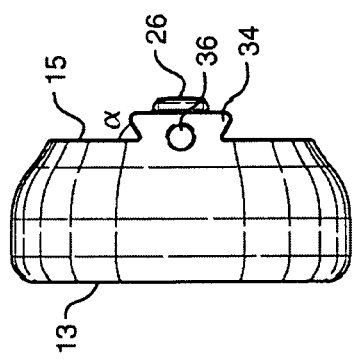
FIGS. 9A-9F, illustrates different views of an embodiment of a head portion of a radial implant according to the present invention.
Figure 9B:
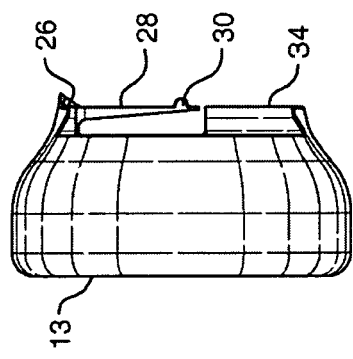
Figure 9A:
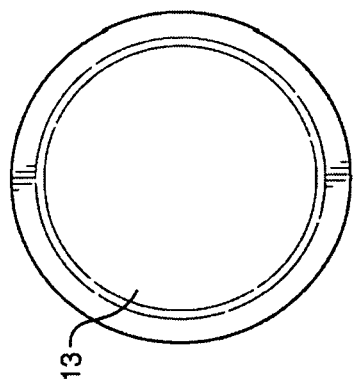
Figure 9F:
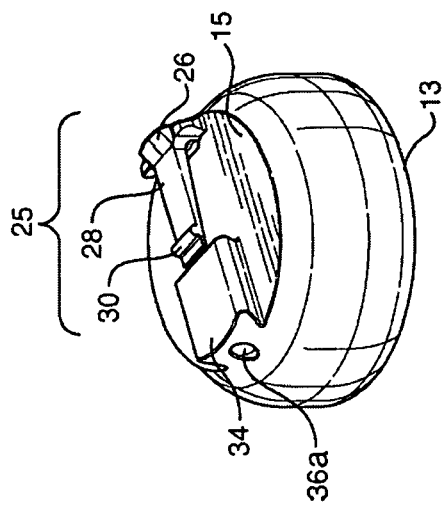
Figure 9E:
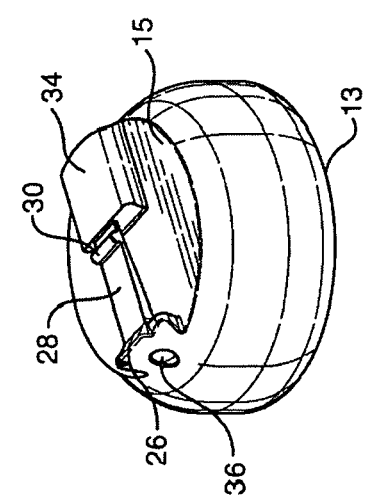
Figure 9D:
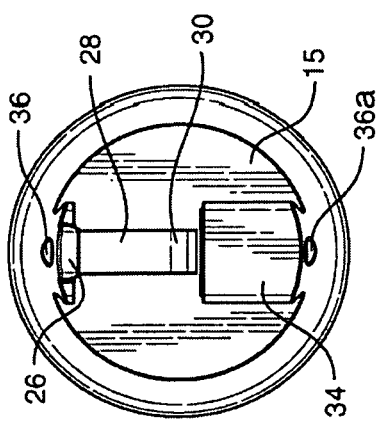
Figure 10B:
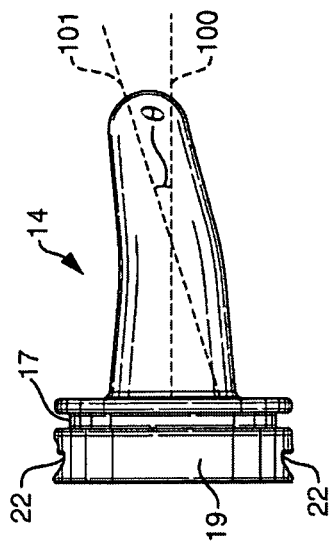
FIGS. 10A-10C, illustrates different views of an embodiment of a stem portion of a radial implant according to the present invention.
Figure 11:
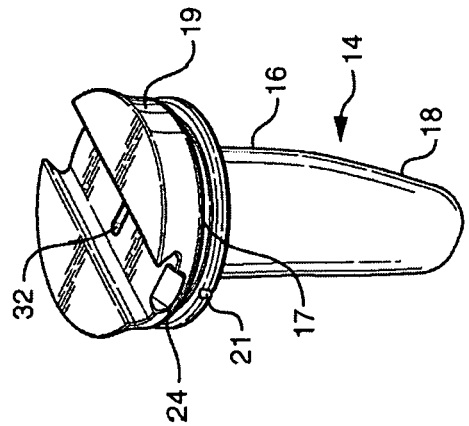
FIG. 11 illustrates an isometric view of an embodiment of a stem portion of a radial implant according to the present invention.
Figure 10A:
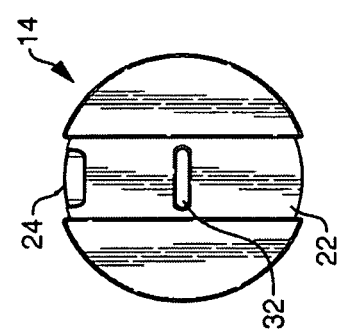
Figure 10C:
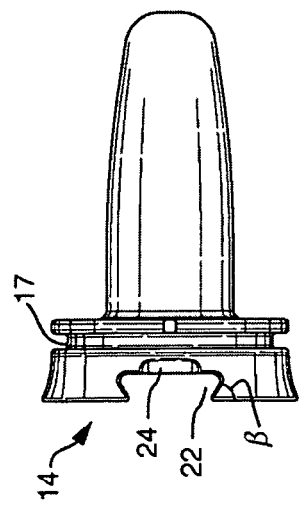

Referring to FIGS. 1 to 5 and 7 to 11, implant 10 comprises a head 12 and a stem 14. In an embodiment of the invention, head 12 is adapted to articulate with the capitellum of a humerus bone. In an embodiment of the invention, head 12 is substantially rounded in shape.

Referring to FIGS. 3 and 4 and 9 and 10, in an embodiment of the present invention, head 12 has a proximal surface 13 that is configured to articulate with the capitellum of a humerus bone. In an embodiment of the invention, proximal surface 13 includes a substantially concave recess to articulate with the capitellum of a humerus bone. In an embodiment of the invention, head 12 also includes a distal surface 15 that includes a mounting portion 20 adapted to engage stem 14 of implant 10. In an embodiment of the invention, head 12 includes a female mating dimple 36, 36a on either side of head 12, substantially 180 degrees from each other, and along the same axis with mounting portion 20, as more fully discussed below.

In an embodiment of the invention, mounting portion 20 is adapted to engage a recessed channel 22 of stem 14. In another embodiment, mounting portion 20 of head 12 is adapted to slideably engage recessed channel 22 of stem 14. In an embodiment of the present invention, mounting portion 20 includes a mating portion 34. In an embodiment of the invention, mating portion 34 is adapted to slideably engage recessed channel 22 along a lateral axis that is substantially 90 degrees from the long axis of implant 10. In an embodiment of the invention, as shown in FIG. 3C, the right and left side portions of mating portion 34 are integral with distal surface 15 of head 12 at an angle, $\alpha$. In another embodiment of the invention the angle, $\alpha$, is equal to or less than 90 degrees. In another embodiment of the invention, as shown in FIG. 3C, the angle, $\alpha$, is preferably less than 90 degrees. In an embodiment of the invention, the angle, $\alpha$, can be the same or different for the right and left side portions of mating portion 34. In an embodiment of the invention, viewed from the side, as in FIG. 4B, the right and left side portions of recessed channel 22 are integral with the proximal side of stem 14 at an angle, $\beta$, that is less than or equal to 90 degrees. In another embodiment of the invention, when mating portion 34 and recessed channel 22 are engaged, $\alpha$ and $\beta$, are substantially equal. In an embodiment of the invention, the angle, $\beta$, can be the same or different for the right and left side portions of recessed channel 22. In an embodiment of the invention, the distal side of mating portion 34 is shaped to slideably engage and conform with recessed channel 22.

In an embodiment of the invention, the mating interaction between recessed channel 22 and mating portion 34 is a dovetail interaction. In an embodiment of the present invention, mounting portion 20 of head 12 comprises a locking mechanism 25, adapted to lockingly engage head 12 with stem 14. In one embodiment of the present invention, locking mechanism 25 comprises an arm 28 and an end tab 26. In an embodiment of the invention, arm 28 is stiff, but slightly flexible or springy. In another embodiment, arm 28 includes a locking tab 30. In an embodiment of the invention, locking tab 30 is adapted to engage a locking tab notch 32 of stem 14. In another embodiment of the invention, end tab 26 is adapted to engage an end notch 24. In one embodiment, stem 14 includes two end notches 24, (see FIGS. 1-5). In one embodiment stem 14 includes one end notch 24, (see FIGS. 7-10). In another embodiment of the invention, when head 12 and stem 14 are fully engaged and locked, end tab 26 engages end notch 24, locking tab 30 engages locking tab notch 32, and head 12 and stem 14 are locked into place.

Referring to FIGS. 4, 5, 10 and 11, in an embodiment of the present invention, stem 14 of implant 10 is substantially perpendicular to recessed channel 22. In an embodiment of the invention, stem 14 is substantially the same width from top to bottom. In another embodiment, stem 14 is tapered. In another embodiment of the present invention, stem 14 is curved in shape and is generally arcuate. In an embodiment of the present invention, the configuration of stem 14 is intended to structurally mimic the shape of the medullary canal of a radius bone.

In one embodiment, stem 14 includes a first stem portion 16 and a second stem portion 18, and a collar 19, which is integral with first stem portion 16. In an embodiment of the invention, collar 19 is positioned to limit insertion of stem 14 into the medullary canal of a radius bone. In another embodiment, the proximal side of collar 19 of stem 14 is integral with recessed channel 22, and at least one end notch 24. In another embodiment, the proximal side of collar 19 includes locking tab notch 32, which, in one embodiment of the invention, is substantially parallel to an end notch 24 along recessed channel 22, and which is adapted to engage locking tab 30 of head 12. In an embodiment of the invention, locking tab notch 32 is located in the center of recessed channel 22. In an embodiment of the invention, collar 19 includes an orientation marker 21, which aids in positioning stem 14 in the medullary canal. In an embodiment of the invention, orientation marker 21 is positioned opposite the biceps tuberosity protrusion. In an embodiment of the invention, recessed channel 22 is positioned along an axis that is substantially parallel to orientation marker 21. In this embodiment, only one end notch 24 is required and head 12 can slideably engage stem 14 from either side; thus this embodiment of implant 10 is useful for both right and left radius bones. In another embodiment, recessed channel 22 is positioned along an axis that is perpendicular to orientation marker 21. This embodiment requires two end notches 24 and will require a right and a left version of implant 10. In another embodiment, collar 19 includes a groove 17, which is adapted to engage an instrument 38 according to the present invention.

In an embodiment of the present invention, first stem portion 16 extends distally from the distal side of collar 19 substantially along a first axis 100. In another embodiment of the present invention, second stem portion 18 extends distally from first stem portion 16 substantially along a second axis 101. In an embodiment of the present invention, the first axis 100 and the second axis 101 define an angle, θ. In one embodiment, the angle θ ranges from about 0 degrees to about 25 degrees. In another embodiment, the angle θ ranges from about 5 degrees to about 25 degrees. In another embodiment, the angle θ ranges from about 5 degrees to about 15 degrees. In an embodiment of the present invention, the curve of stem 14 that is established by the angle, θ, can be achieved using a radius of curvature that is in a range of from about 0.5 inch to about 3 inches. In another embodiment of the present invention, the curve of stem 14 that is established by the angle, θ, can be achieved using a radius of curvature that is in a range of from about 0.5 inch to 3 inches or from about 1 inch to about 2.5 inches. In another embodiment, the curve of stem 14 that is established by the angle, θ, can be achieved using a radius of curvature that is in a range of from about 1.5 inches to about 2 inches. In an embodiment of the present invention, recessed channel 22 is positioned along a third axis that is substantially perpendicular to the first axis 100 of stem 14.

In another embodiment of the present invention, the cross section of stem 14 decreases (for example, as a taper) as it extends distally from head 12. In an embodiment of the invention, the taper of stem 14 facilitates insertion of stem 14 into the medullary canal of the radius bone and aids to anchor implant 10 to the radius bone. In another embodiment, the cross section of stem 14 remains constant as it extends distally from head 12. In an embodiment of the present invention, stem 14 is substantially identical to the stem portion of the radial implant disclosed in U.S. Pat. No. 6,709,459, which is herein incorporated by reference in its entirety. In another embodiment, stem 14 is substantially identical to the stem portion of the radial implant disclosed in U.S. Pat. No. 6,656,225, which is herein incorporated by reference it its entirety.

In an embodiment of the invention, stem 14 is cemented, press fit, and/or impacted into the intramedullary canal according to methods known by those skilled in the art. In an embodiment of the invention, a cement, for example, methyl methacrylate, is used.

In an embodiment of the present invention, radial implant 10 includes a roughened or textured surface on part or all of implant 10 that interacts with the medullary canal of the radius bone to aid in securing stem 14 to the radius bone and to allow for bone ingrowth. In an embodiment of the present invention, stem 14 may be coated with a material such as titanium, cobalt-chrome beads, or hydroxyapatite.

In an embodiment of the present invention, radial implant 10 is comprised of any medically acceptable, biocompatible implant material. In one embodiment, radial implant 10 is comprised of cobalt chrome. In one embodiment, the cobalt chrome is highly polished. In another embodiment, radial implant 10 is comprised of titanium. In another embodiment, radial implant 10 is comprised of durable, biocompatible plastic or polymer material. In another embodiment, radial implant 10 is comprised of stainless steel. In another embodiment, radial implant 10 is comprised of ceramic material.

Figure 6B:
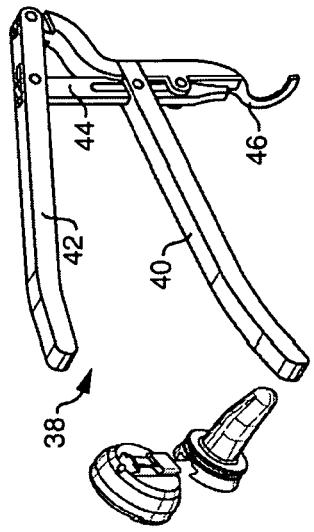
FIGS. 6A-6D, illustrates different views of an instrument according to the present invention.
Figure 6D:
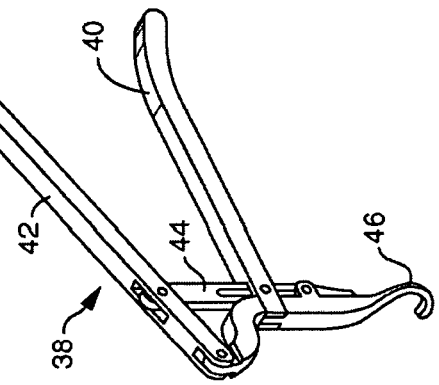
Figure 6A:
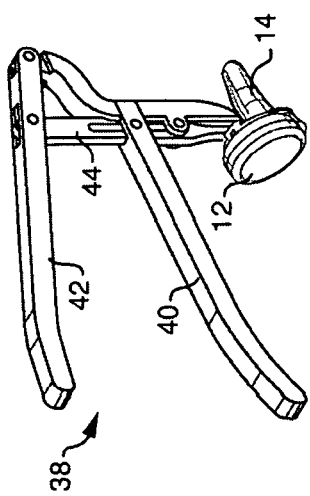
Figure 6C:
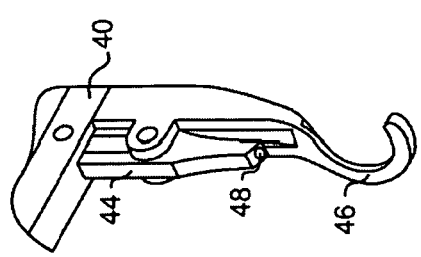

The present invention also relates to an instrument for implanting or removing the lateral radial head implant. Referring to FIG. 6, in an embodiment of the invention, instrument 38 includes a fixed handle 40, a movable handle, 42, a sliding lever 44, and a hook mechanism 46. In an embodiment of the invention, sliding lever 44 further includes a male mating portion 48 to engage female mating portion 36, 36a of head 12.

The present invention is also directed to methods for using and implanting radial implant 10. In an embodiment of the present invention, implant 10 is assembled by engaging head 10 with stem 14. In an embodiment of the invention, recessed channel 22 is adapted to engage head 12 with stem 14. In an embodiment of the present invention, when head 12 engages stem 14, mating portion 34 slides into recessed channel 22 of stem 14. In an embodiment of the invention, mating portion 34 slides into recessed channel 22 of stem 14 by way of a dovetail mating mechanism. In an embodiment of the invention, mating portion 34 slides into recessed channel 22 from either the right or left side of stem 14, depending on which (i.e., the right or the left) radial head is being replaced. In another embodiment of the invention recessed channel 22 includes a single end notch 24 and recessed channel 22 is rotated 90 degrees relative to orientation marker 21. Accordingly, in this embodiment of the invention, when head 12 fully engages stem 14, mating portion 34 slides into position in recessed channel 22, locking tab 30 snaps into notch 32, and end tab 26 engages the single end notch 24 on stem 14. In another embodiment of the invention, recessed channel 22 includes two end notches 24. Accordingly, in this embodiment of the invention, when head 12 fully engages stem 14, mating portion 34 slides into position in recessed channel 22, locking tab 30 snaps into notch 32, and end tab 26 engages one of end notches 24 on stem 14. In an embodiment of the invention, end notch 24 engages with end tab 26 as mating portion 34 slideably engages recessed channel 22.

In an embodiment of the invention, the proximal surface of end notch 24 is angled upward such that locking mechanism 25, in particular arm 28, upon engagement of end notch 24, moves to a depressed state as head 12 slides into recessed channel 22. In one embodiment, head 12 slides into recessed channel 22 from either end of recessed channel 22. In another embodiment of the invention, head 12 slides into recessed channel 22 from one end of recessed channel 22. In an embodiment of the invention, when locking tab 30 reaches notch 32, locking tab 30 and arm 28 spring into an extended state and locking tab 30 locks into place at notch 32. In another embodiment of the invention, end tab 26 is angled downward and is adapted to mate with end notch 24 when head 12 and stem 14 are fully engaged.

In an embodiment of the invention, instrument 38 is used as an insertion tool to aid in inserting stem 14 into the medullary canal of the radius bone. In an embodiment of the invention, hook mechanism 46 engages groove 17 of stem 14. In an embodiment of the invention, stem 14, engaged with instrument 38, is implanted into a patient. In an embodiment of the invention, once stem 14 is implanted, head 12 is implanted by aligning male mating portion 48 of sliding lever 44 with female mating portion 36 of head 12 and applying opposing manual or mechanical pressure to fixed handle 40 and movable handle 42 (i.e., squeezing together) such that male mating portion 48 of sliding lever 44 engages female mating portion 36 of head 12. In an embodiment of the invention, head 12 slideably engages stem 14 until locking tab 32 on head 12 engages notch 30 of stem 14 and locks into place. In another embodiment of the invention, stem 14 is implanted prior to engagement with hook mechanism 44.

In an embodiment of the present invention, head 12 is adapted to unlock and disengage from stem 14. In an embodiment of the invention, head 12 is disengaged from stem 14 using instrument 38. In an embodiment of the invention, instrument 38 is rotated 180 degrees from its implant position (shown in FIG. 6A). In an embodiment of the invention, hook mechanism 44 engages groove 17 of stem 14. In an embodiment of the invention, head 12 is disengaged from stem 14 by aligning male mating portion 48 of sliding lever 44 with female mating portion 36a of head 12 and applying opposing manual or mechanical pressure to fixed handle 40 and movable handle 42 (i.e., squeezing together) such that male mating portion 48 of instrument 38 engages female mating portion 36a of head 12. In an embodiment of the invention, the pressure to fixed handle 40 and movable handle 42 disengages locking tab 30 from notch 32 and mounting portion 20 of head 12 slides out of recessed channel 22 and off of stem 14. In an embodiment of the invention, the pressure applied to fixed handle 40 and movable handle 42 must be great enough to overcome the normal kinematic forces generally encountered at the elbow joint. In another embodiment of the invention, the pressure applied to fixed handle 40 and movable handle 42 must be great enough to overcome up to twice the normal kinematic forces generally encountered at the elbow joint. In another embodiment of the invention, the pressure applied to fixed handle 40 and movable handle 42 must be great enough to overcome up to five times the normal kinematic forces generally encountered at the elbow joint.

It should be understood that the invention is not to be limited to the specific conditions or details described herein. Throughout the specification, any and all references to a publicly available document, including but not limited to a U.S. patent, are specifically incorporated by reference.

It will be apparent to those skilled in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

What is claimed is:

1. A radial head implant for replacement of a head portion of a radius bone comprising:
 a head having a proximal surface including a substantially concave recess configured to articulate with a capitellum of a humerus bone;
 a stem; and
 a locking mechanism configured to secure said head to said stem when said head is fully engaged with said stem, said locking mechanism comprising:
  a longitudinal channel having a first end, a second end, an end notch disposed at the second end, and a tab notch disposed at a position between the first end and the second end;
  a mating portion engageable with the longitudinal channel in a dovetail interaction such that the mating portion is positioned in the longitudinal channel between the first end and the tab notch when the head is secured to the stem; and
  an elongate spring arm having a longitudinal axis, a locking tab and an end tab, each of the locking tab and the end tab protruding from a first surface of the spring arm in a direction that is substantially transverse to the longitudinal axis, and wherein said end notch is adapted to engage said end tab and said tab notch is adapted to engage said locking tab when the head is secured to the stem.

2. The radial head implant of claim 1, wherein said head is also adapted to disengage said stem.

3. The radial head implant of claim 1, wherein said head is adapted to slidably engage said stem.

4. The radial head implant of claim 1, wherein said stem has (1) a proximal end and a distal end, (2) a first portion extending distally from said proximal end and substantially along a first axis, and (3) a second portion extending distally from said first portion and substantially along a second axis to said distal end, said first axis and said second axis defining an angle therebetween, said stem being shaped to facilitate insertion of said stem into the medullary canal of the radius bone and wherein the longitudinal axis is substantially transverse to the first axis when the head is engaged with the stem.

5. The radial head implant of claim 4, wherein said angle is from about 0 degrees to about 25 degrees.

6. The radial head implant of claim 4, wherein said angle is from about 5 degrees to about 25 degrees.

7. The radial head implant of claim 4, wherein a radius of curvature therebetween said first portion and said second portion is in a range between about 0.5 inches and about 3 inches.

8. The radial implant of claim 1, wherein said stem is tapered with a distally decreasing cross section to facilitate insertion of said stem into the medullary canal of the radius bone.

9. The radial head implant of claim 1, wherein the spring arm is disposed within the longitudinal channel from the tab notch to the second end when the head is secured to the stem.

10. The radial head implant of claim 1, wherein said head comprises said mating portion and said stem comprises said longitudinal channel.

11. The radial head implant of claim 1, wherein the spring arm comprises a cantilever having a fixed end and a free end, wherein the end tab is positioned proximate the fixed end, and wherein the locking tab is positioned proximate the free end.

12. A radial head implant of claim 11, wherein the fixed end is fixed to the head component proximate a periphery of the head component and the free end is proximate a center of the head component.

13. A radial head implant comprising:
 a head component having proximal surface including a substantially concave recess configured to articulate with a capitellum of a humerus bone;

a stem component engageable with the head component; and a securement configured to lock an unlock the stem component to the head component, the securement including:

a longitudinal channel having a first end, a second end, an end notch disposed at the second end, and a tab notch disposed at a position between the first end and the second end;

a mating portion engageable with the longitudinal channel in a dovetail interaction such that the mating portion is positioned in the longitudinal channel between the first end and the tab notch when the head component is locked to the stem component; and a cantilever spring arm disposable within the longitudinal channel such that the cantilever spring arm extends substantially along a centerline of the longitudinal channel from the tab notch to the second end when the head component is locked to the stem component, the cantilever spring arm having an end tab, proximate a fixed end of the cantilever spring arm, that is configured to be received in the end notch and having a locking tab, proximate a free end of the cantilever spring arm, that is configured to be received in the tab notch when the end tab is received in the end notch, each of the end tab and the locking tab protruding from the cantilever spring arm in a direction that is substantially transverse to the longitudinal channel when the head component is secured to the stem component.

14. The radial head implant of claim 13, wherein the longitudinal channel is disposed on the stem component, the mating portion is disposed on the head component, and the cantilever spring arm is disposed on the head component.

15. The radial head implant of claim 14, wherein the fixed end of the cantilever spring arm is positioned proximate a periphery of the head component and the free end of the cantilever spring arm is positioned proximate the mating portion.

16. The radial head implant of claim 13, wherein the tab notch is disposed proximate a center of the longitudinal channel.

17. The radial head implant of claim 13, wherein the fixed end of the cantilever spring arm is positioned proximate a periphery of the head component and the free end of the cantilever spring arm is positioned proximate the mating portion.

18. The radial head implant of claim 13, wherein the mating portion and cantilever spring arm are symmetric about a common plane.

19. The radial head implant of claim 13, wherein the mating portion of the securement is a first mating portion and the securement further comprises a second mating portion engageable with the channel in a dovetail configuration at an opposite end of the channel from the first mating portion.

20. The radial head implant of claim 19, wherein the cantilever spring arm is disposed between the first mating portion and the second mating portion.

21. The radial head implant of claim 20, wherein the fixed end of the cantilever spring arm is fixed to the second mating portion and the free end of the cantilever spring arm is proximate the first mating portion.

22. The radial head implant of claim 13, wherein the mating portion protrudes from a distal end of the head component and includes a surface that extends from a distal face of the head component at an angle that is less than 90 degrees.

23. The radial head implant of claim 13, wherein the mating portion protrudes from a distal end of the head component and includes a plurality of surfaces that extend from a distal face of the head component and each of the plurality of surfaces extend from the distal face at an angle that is less than 90 degrees.

24. The radial head implant of claim 13, wherein the tab notch is located along the centerline of the longitudinal channel.

25. The radial head implant of claim 13, wherein each of the locking tab and the end tab protrude from a first surface of the cantilever spring arm.

26. The radial head implant of claim 13, wherein the locking tab and the tab notch are configured so that the locking tab snaps into the tab notch as the head component fully engages the stem component.

27. The radial head implant of claim 13, wherein the tab notch and the end notch are each disposed about substantially parallel longitudinal axes.

28. The radial head implant of claim, 13, wherein the end notch is configured to urge the cantilever spring arm to a depressed state as the head component engages the stem component.

29. The radial head implant of claim 13, wherein the locking tab and the tab notch are engagable when the securement is in a locked state and the securement is configured to migrate from the locked stated to an unlocked state by the application of opposing pressures applied to the head component and the stem component.

30. The radial head implant of claim 13, wherein the cantilever spring arm is tapered from the fixed end to the free end.

* * * * *